US008293258B2

(12) United States Patent
Probasco et al.

(10) Patent No.: US 8,293,258 B2
(45) Date of Patent: *Oct. 23, 2012

(54) PESTICIDE TREATMENTS MADE FROM HOP EXTRACTS

(75) Inventors: Gene Probasco, Yakima, WA (US); Mark M. Bossert, Yakima, WA (US); David W. Hysert, Yakima, WA (US)

(73) Assignee: John I. Hass, Inc., Washington, DC (US)

( * ) Notice: Subject to any disclaimer, the term of this patent is extended or adjusted under 35 U.S.C. 154(b) by 973 days.

This patent is subject to a terminal disclaimer.

(21) Appl. No.: 11/008,781

(22) Filed: Dec. 8, 2004

(65) Prior Publication Data

US 2005/0220914 A1     Oct. 6, 2005

Related U.S. Application Data

(63) Continuation-in-part of application No. 10/805,876, filed on Mar. 22, 2004, which is a continuation-in-part of application No. 10/212,982, filed on Aug. 5, 2002, now abandoned, which is a continuation of application No. 09/573,332, filed on May 17, 2000, now abandoned.

(51) Int. Cl.
*A01N 25/32* (2006.01)
*A01N 25/02* (2006.01)
*A01N 65/00* (2009.01)

(52) U.S. Cl. ........ 424/406; 424/405; 424/725; 424/750; 514/678; 514/689; 514/690

(58) Field of Classification Search ........................ None
See application file for complete search history.

(56) References Cited

U.S. PATENT DOCUMENTS

| | | | |
|---|---|---|---|
| 3,615,660 A | 10/1971 | Bavisotto et al. | |
| 3,886,171 A * | 5/1975 | Parsons | 546/309 |
| 4,148,873 A | 4/1979 | Owades | |
| 4,170,638 A | 10/1979 | Owades | |
| 5,227,162 A | 7/1993 | Ferrari et al. | |
| 5,372,817 A * | 12/1994 | Locke et al. | 424/405 |
| 5,827,895 A | 10/1998 | Nutter et al. | |
| 6,096,350 A | 8/2000 | Kemp et al. | |
| 6,204,283 B1 | 3/2001 | Black et al. | |
| 6,379,720 B1 * | 4/2002 | Cooper et al. | 424/778 |
| 6,646,014 B2 | 11/2003 | Watkins et al. | |
| 6,702,645 B2 | 3/2004 | Vanderpool | |
| 7,597,912 B2 * | 10/2009 | Probasco | 424/737 |
| 2001/0014346 A1 | 8/2001 | Watkins | |
| 2002/0051804 A1 | 5/2002 | Probasco et al. | |
| 2003/0060379 A1 | 3/2003 | Souter et al. | |
| 2004/0091558 A1 * | 5/2004 | Lutz et al. | 424/745 |
| 2005/0043404 A1 | 2/2005 | Probasco et al. | |
| 2005/0049230 A1 | 3/2005 | Henrich et al. | |
| 2005/0220914 A1 | 10/2005 | Probasco et al. | |
| 2006/0009122 A1 | 1/2006 | Swanson | |
| 2006/0013870 A1 | 1/2006 | Kuhrts | |

FOREIGN PATENT DOCUMENTS

GB        2330076        4/1999

OTHER PUBLICATIONS

Jones, G., "Potential Control of Two-Spotted Spider Mite, *Tetranychus urticae* Koch, Using Hop β-Fraction," (1998) pp. 1-165, A thesis submitted for the degree of Doctor of Philosophy of the Univeristy of London and for the Diploma of Imperial College of Science, Technology & Medicine.

"Culpeper's Complete Herbal A book of Natural Remedies for Ancient Ills" Wordsworth Reference, pp. 134-135 (1995).

Losel et al., The Potentional of Semidochemicals for Control of *Phorodon hummuli* (Homoptera: aphididae), Pesticide Science, vol. 48, No. 4, pp. 293-303 1996.

Jones et al., "Repellant and Oviposition-Deterring Effects of Hop-Beta Acids on the Two-Spotted Spider Mite *Tetranychus urticae*," Pesticide Science, vol. 47, No. 2, pp. 165-169 (1996).

* cited by examiner

*Primary Examiner* — Neil Levy

(74) *Attorney, Agent, or Firm* — Edwards Wildman Palmer LLP; Jeffrey D. His, Esq.; Melissa Hunter-Ensor, Esq.

(57) ABSTRACT

The invention is an organic pesticide made from components of hop extract by preparing stable aqueous emulsions of hop acids and other hop extract components. The hop acids and other hop extract components are suspended as stable, colloidal preparations in water, which can be sprayed on plants for pest control.

12 Claims, 1 Drawing Sheet

PESTICIDE TREATMENTS MADE FROM HOP EXTRACTS

RELATED APPLICATIONS

This specification is a continuation-in-part of application Ser. No. 10/805,876, filed Mar. 22, 2004. Application Ser. No. 10/805,876 is a continuation-in-part of application Ser. No. 10/212,982, filed Aug. 5, 2002, now abandoned. Application Ser. No. 10/212,982 was a continuation of application Ser. No. 09/573,332, filed May 17, 2000, now abandoned.

TECHNICAL FIELD

The invention disclosed here generally relates to acaricides and fungicides. More particularly, it relates to the use of hop extracts as an acaricide and fungicide for the treatment of plant pests.

BACKGROUND OF THE INVENTION

Chemical pesticides are used in commercial agriculture, home gardening, residential use, and similar applications for the purpose of controlling insects and various kinds of plant diseases. There are well-known environmental and health concerns associated with the use of these kinds of chemicals. In some instances, it has been proven that the long-term use of certain chemical pesticides creates environmental problems. A well-known example involves the ban of DDT in the United States.

Ongoing health concerns about the agricultural and home use of chemicals have given rise to an emerging market for more "organic" or "green" treatments for pests and plant diseases. Organic treatments do not involve the use of strong, synthetically-produced chemicals. Insecticidal soap is one example of what many consider to be an organic or organic-like pesticide that is in use today.

With respect to pesticides, known organic treatments are generally deemed to be less effective than chemical pesticides. There is a trade-off when comparing one to the other. Chemical pesticides have a higher level of toxicity and therefore provide better pest control. On the other hand, higher toxicity also heightens environmental concerns. The same level of environmental concern does not attach to organic pesticides, but at the price of less-effective pest control.

Figure 1:
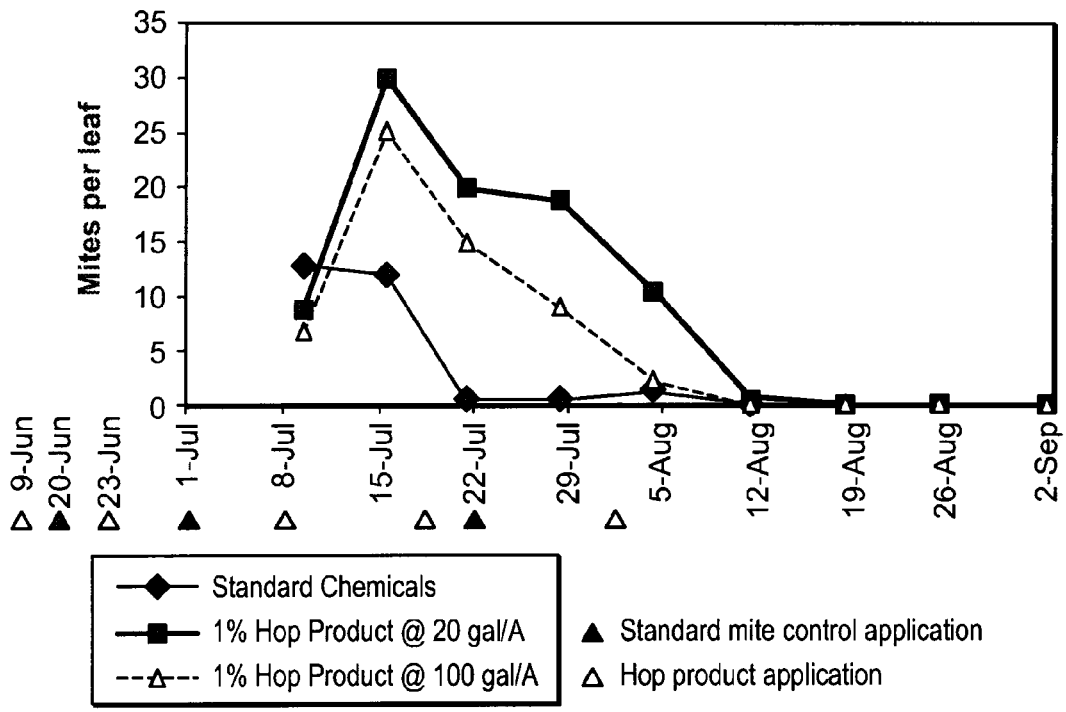
FIGS. 1 and 2 are graphs showing that hop acids control spider mites in hop fields.
Figure 2:
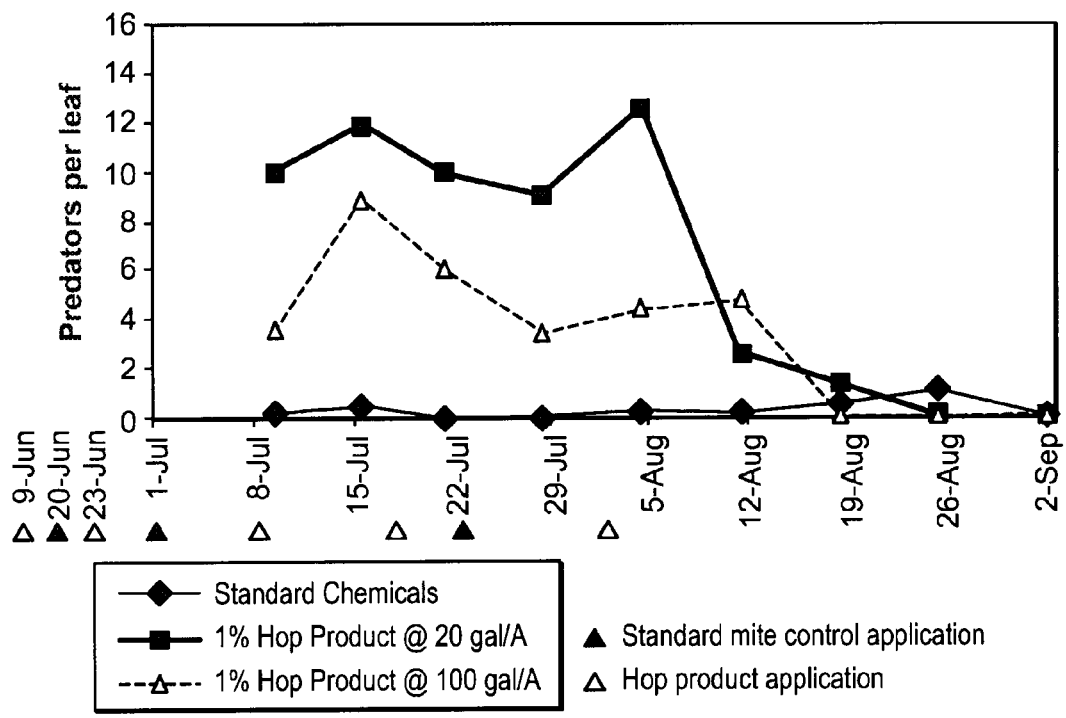

The invention disclosed below relates to the use of hop extracts as an organic treatment for plant pests. Hop cones contain lupulin glands that have two important bittering substances: alpha acids and beta acids. These acids are sometimes called humulones and lupulones, respectively. Hop acids were initially used as a plant-derived preservative agent for beer, prior to the existence of refrigeration. Today, they are primarily used to create the bitter taste and flavor of beer.

For the purposes of this disclosure, the term "hop acids" means alpha acids, beta acids, mixtures of these acids, and/or other components found in hop extracts, such as beta fraction, essential oils, waxes, and uncharacterized resins, as well as all forms of modified hop acids, such as isoalpha acids, tetrahydroisoalpha acids, rhoisoalpha acids, hexahydroisoalpha acids, and hexahydrobeta acids. As is well known, alpha acids consist of mixtures of analogues, primarily humulone, cohumulone, adhumulone, and other minor constituents. Similarly, beta acids consist of mixtures of analogues, primarily lupulone, colupulone, adlupulone, and other minor constituents. For these reasons, alpha and beta acids are referred to in the plural.

Also, for the purposes of this disclosure, the term "pests" should be taken to mean insect and non-insect pests. For example, it is meant to include spider mites and other insects. It is also meant to include powdery mildews, downy mildews, early and late blight organisms, and other kinds of plant diseases.

A number of companies are in the business of producing hop extracts for the brewing industry. These extracts come from the hops that are grown in various regions of the world. In some respects, the hop extract industry is a combination of agriculture and chemistry. On the agricultural side, hop growers have many of the same kinds of problems with plant pests as the growers of other food products. For example, spider mites (*Tetranychus urticae*), which are a common agricultural and home garden pest, are also a problem for hop growers. Many agricultural crops and home garden plants are also affected by various species of the powdery mildew fungus, molds, and other kinds of blights or diseases. Powdery mildew is particularly a problem for hop growers and wine grape growers.

Given that people have been essentially drinking hop acids as a component of beer for many centuries, hop acids are a proven organic consumable. Hops are regarded as one of the basic ingredients of beer and, as such, hops and hop extracts are considered GRAS (Generally Recognized As Safe) by the U.S. Food and Drug Administration ("FDA").

Those who work with hop extracts have discovered that the beta fraction of hop acids dissolved in ethanol or xylene can be toxic to spider mites. Given that hop extracts are recognized as safe for humans, this creates potential uses for hop extracts as a "green" or organic pesticide. However, there are problems associated with delivering hop extracts as a plant spray containing xylene or ethanol—which is the best delivery carrier for applying treatments to plant leaves.

While hop acids are highly soluble in solvents like ethanol or xylene, these carrier agents are not organically sound for spraying on plants in an agricultural or home garden setting. Agricultural sprays are usually applied at the rate of many gallons per acre. One can imagine that environmental concerns arise if large quantities of ethanol or xylene are sprayed on field crops. Moreover, while an ethanol or xylene-based spray of hop acids might be effective against mites, these carrier agents, if improperly applied, might do direct harm to the plant leaves, regardless of any beneficial mite-controlling effects.

As with most chemical pesticide applications today, water is the carrier of choice for spray application on fields and in the home garden. However, creating a water-based spray of hop acids is not immediately feasible because, unlike solvents like ethanol and xylene, hop acids are not highly soluble in water. Because they are weak organic acids, they can be dissolved in water if the pH is raised above normal pH ranges and maintained at levels above the pKa levels of the acids. The pKas of hop acids range from 5-9. Therefore, stable aqueous solutions of hop acids can be produced at pHs ranging from 7-11 and higher. In contrast, the pH of chemical sprays is generally below 7. If the pH of a chemical spray becomes considerably higher than 7 or lower than 5, then it raises concerns about effectiveness and doing harm to plant leaves. It is difficult to maintain a stable aqueous solution of hop acids within the lower pH range that is desirable for sprays. As a consequence, while water is an essential carrier for treating plants, because of solubility problems, water is not easy to use as a carrier, if hop acids are the active agent in the plant treatment.

The present invention provides a way to use water as the carrier for delivering hop acids as a pesticide spray for certain plant pests. Moreover, the present invention provides potentially useful treatments for control spider mites, powdery mildews, downy mildews and late blights.

SUMMARY OF THE INVENTION

The invention is a treatment formulation made from hop acids and related hop extract components that can be used as a pesticide for control of spider mites, powdery mildews, downy mildews and late blights. The treatment formulation is produced by creating an aqueous emulsion of hop acids. An "emulsion" is different from a "solution" and enables hop acids and other hop extract components to be applied to plants as a component of a water-based spray, rather than using a non-aqueous solvent. Emulsions are essentially colloidal suspensions of small globules of one liquid in a second liquid, with no mixture in the sense of one substance dissolving into another.

As discussed above, hop acids are not highly soluble in water. However, stable aqueous solutions of certain hop acids can be prepared by the selection of appropriate concentration and pH. Further, it is possible to convert these solutions into stable aqueous emulsions (i.e., colloidal suspensions in water) that will not separate over time, with the added advantage that the emulsions can be diluted with water, as required, by the end user for spraying onto plants for pest control.

Although the emulsions are stable, they are also susceptible to film or residue creation when diluted with hard water. Films are problematical with spray applicators in the field because they clog spray nozzles. Regardless of the effectiveness of the treatment formulation as an active agent in controlling plant pests, if the solution cannot be applied effectively because of nozzle clogging, then it is essentially useless. The film or residue problem can be eliminated by adding liquid soap to the treatment solution at a low concentration of approximately 0.5%.

We have been engaged in the ongoing development of hop acid formulations for use as treatment formulations for plant pests. Our initial formulations involved experimenting with 10% solutions of hop acids diluted with water to create stable aqueous emulsions. The initial studies involved the preparations and efficacy testing of emulsions from beta acids and alpha acids. Subsequent work involved field studies using beta acid emulsions with the concentration reduced from 10% to 1%. These efforts have led to a useful way to apply hop acids as a treatment agent. Moreover, they have led to the development of plant treatments that are believed to be effective against certain kinds of plant pests.

BEST MODE FOR CARRYING OUT THE INVENTION

A. Initial Tests Involving 10% Solutions of Hop Acids.

The following descriptions set forth examples for creating stable 10% solutions of hop acids that can be converted into stable emulsions by subsequent dilution with water. The 10% solutions can be diluted to lesser concentrations as desired to produce stable aqueous emulsions that are usable as a spray-on plant treatment. These treatment emulsions are believed to have potential use as pesticides. The initial tests demonstrated that the diluted emulsions remain stable at all dilutions and this means that the concentrated solutions can be sold as organic pesticides and later diluted by the user.

We initially developed two basic test formulations. These formulations involved the preparation of 10% solutions of alpha and beta acids that were converted to stable, aqueous emulsions upon the addition of water. Specific examples of these formulations are set forth below.

1. Preparation of 10% Aqueous Beta Acids Solution.

General Example:

Beta fraction was the starting material used to initially prepare a 10% aqueous beta acids solution. The term "beta fraction" refers to the oily, waxy, resinous portion of a hop extract obtained when the hop extract is washed with caustic water to remove most of the alpha acids. The beta fraction contains mostly beta acids, resins, oils, and waxes. It is also called beta acid oil. The beta fraction may be used, as is, or washed with caustic water to reduce the alpha acids concentration in the beta fraction so that the ratio of alpha acids to beta acids is 0.05, or below, by HPLC analysis. The temperature of the beta fraction was raised to 60° C. with continuous mixing, and caustic was added in the form of KOH to bring the pH to 10-11. Having first determined the beta acids content in the beta fraction by HPLC analysis, a volume of 60° C. water was added, while mixing, so that the beta acids concentration of the aqueous phase was between 10% and 50%. The pH of the solution was adjusted, if necessary, to 10-11 at 60° C. It was necessary to subtract the volume of KOH added for pH adjustment from the calculated volume of water. Also, a temperature range of 55-70° C. was acceptable, although 60° C. was optimal. Mixing was stopped, and the mixture was allowed to sit for at least 45 minutes, during which time the temperature of the solution was maintained at 60° C. The aqueous beta acids phase was then separated from the resinous phase. The aqueous beta acids phase was diluted to a concentration of 10% beta acids by HPLC, while the temperature was maintained at 60° C., and the pH kept at 10-11. The aqueous phase was cooled (mixing is optional) to 1-13° C., and allowed to sit for at least 2 hours. The solution was then decanted or filtered.

Small-Scale 10% Aqueous Beta Acids Solution Example:

500 g of beta fraction containing 50% beta acids by HPLC was heated to 60° C. Approximately 250 mL of 20% KOH was added, while stirring with heat to maintain a 60° C. temperature, and to bring the pH up to 10.7. Mixing was stopped, and the mixture was allowed to sit overnight. The following morning, the resinous fraction was set aside and the aqueous fraction was heated to 60° C. and analyzed by HPLC. Water and 20% KOH were added to bring the beta acids concentration to 10%, and the pH to 10.7. The aqueous beta acids solution was refrigerated to 5° C. overnight, and filtered the next morning.

Large-Scale 10% Aqueous Beta Acids Solution Example:

1000 kg of beta fraction at 60° C. was placed in a hot water-jacketed tank. Approximately 120 gallons of 20% KOH were added with continuous mixing until the pH of the aqueous phase reached 10.7. The mixing was shut down, but the heat was maintained at 60° C., and the mixture was allowed to sit overnight. The aqueous layer was pumped into a stainless steel, heat-jacketed tank and diluted to a 10% beta acids concentration by HPCL using deionized water. The temperature and pH were maintained at 60° C. and 10.7, respectively. Heating of the tank was stopped, the product was cooled to 10° C., and then allowed to settle overnight. Clouded and precipitated material was pumped to a recycle tank, and the clear beta acids solution was filtered.

2. Preparation of 10% Aqueous Alpha Acids Solution.

General Example:

Supercritical $CO_2$ extract was used to prepare a 10% aqueous alpha-acids solution. The hop extract was placed in a volume of water calculated to produce an aqueous alpha acids solution, with a concentration of 3-20% by HPLC. An alpha acid concentration of less than 8% was optimum. At this concentration, beta acid solubility in the aqueous phase was lowered. The temperature was raised to 50-70° C., and the pH was adjusted to 6-8, with constant mixing. A pH of 7-8 was optimum. The extract solution was then allowed to sit for at least 45 minutes. The resinous fraction containing beta-acids, oils, and waxes was set aside, while the aqueous alpha-acids solution was decanted. The temperature was raised to 60° C. and the pH was raised to 7-9. The solution was analyzed by HPLC. If the alpha-acids concentration was 10% or greater, water was added to bring the concentration to 10%. The solution was cooled to 1-19° C., and filtered or decanted.

If the alpha acids concentration was less than 10%, the aqueous solution was acidified ($H_2SO_4$ or $H_3PO_4$ were satisfactory) at 60° C. to bring the alpha acids out of solution. The alpha acids were washed with fresh 60° C. water and allowed to sit for a minimum of 45 minutes. The water was discarded, and a calculated volume of 60° C. fresh water was added. The volume was calculated to produce a 10% alpha acid concentration by HPLC, also taking into account the volume of caustic necessary for pH adjustment. The alpha acids solution was heated to 60° C., and the pH was raised to 7-9 with KOH solution, as necessary. The aqueous solution was allowed to cool to 1-19° C., and filtered or decanted.

Small-Scale 10% Aqueous Alpha Acids Solution Example:

800 g of supercritical $CO_2$ extract was added to 2700 mL of deionized water, and the temperature was increased to 60° C., with constant mixing. Approximately 300 mL of 20% KOH was added to bring the pH up to 7.7. The solution was allowed to sit overnight. The resinous fraction containing beta acids, oils, and waxes was set aside, while the aqueous alpha-acids solution was decanted and cooled overnight to 7° C. The aqueous solution was then filtered, while cold, to remove any crystallized beta fraction, and brought back to 60° C. 20% $H_2SO_4$ was added with continuous stirring until the pH was 2.5. The resinous alpha acids were separated and washed with fresh 60° C. deionized water. The alpha acids were added to 2000 mL deionized water and brought to 60° C. Approximately 300 mL of 20% KOH were added to bring the pH up to 8.0, and the solution was analyzed by HPLC. Deionized water and 20% KOH were added to bring the concentration and pH up to 10% and 8.9, respectively. The solution was cooled to 5° C. overnight, and filtered.

3. Creation of Emulsions from 10% Aqueous Beta Acids and Alpha Acids Solutions.

10% aqueous beta acids solutions and 10% aqueous alpha acids solutions are clear with no precipitated material. They are similar to weak iced tea in color, clarity, and consistency. Dilutions of these 10% solutions with tap or well water result in the formation of stable aqueous emulsions which have the appearance of pineapple juice and do not exhibit any separation even after days of storage. They are very stable, and precipitate does not form even down to a dilution of 1:16. Also, as these solutions are diluted with water, pH drops by about 0.5 pH units but not enough to cause precipitation.

4. Initial Methods of Application

Tests were conducted to determine the efficacy of hop acids for the control of the twospotted spider mite, powdery mildew and downy mildew diseases on hop plants, late blight disease on potato plants, and powdery mildew disease on wine grape plants. Preparations of the 10% aqueous alpha acids solution and the 10% aqueous beta acids solution were diluted with tap water to make emulsions of lower concentrations for testing.

The alpha acids and beta acids emulsions described previously in section three were sprayed on test plants in the greenhouse and laboratory using a hand-held and manually-operated bottle sprayer of 500 mL volume, with finger lever action and nozzle adjusted to the finest droplet size. Application of each formulation consisted of two pulls of the sprayer lever with the nozzle 12 inches from the leaf surface. Each double pull of the lever applied approximately 2 milliliters of liquid to an area of approximately one square foot. The spray pattern did not provide droplet density sufficient to cover 100% of the leaf area, but droplets were close enough to each other to cover about 50% of the leaf area. Treated hop leaves were placed inside a growth chamber or greenhouse at approximately 22 degrees centigrade.

5. Initial Results

The following sections detail the results of the initial tests for efficacy of hop acids against certain pests.

Hop Powdery Mildew Control Tests

The hop powdery mildew organism is the fungus *Podosphaera macularis* and the host plant is hop, *Humulus lupulus*. Tests were conducted in a greenhouse near Toppenish, Wash. Young hop plants with eight pairs of leaves were used for testing. Test plants were sprayed with treatment using a spray bottle with a pull trigger. After the treatment dried, powdery mildew spores suspended in water were sprayed onto the test leaves with a spray bottle. Inoculated plants were incubated in a greenhouse for seven days and then lesions were counted on one pair of leaves per plant. Treatments were replicated four times. Standard control was the fungicide Myclobutanil (Rally). Percent incidence is the average number of lesions per leaf on ten hop leaves expressed as a percent of the untreated control.

| Treatment | Percent Incidence | Percent Concentration |
| --- | --- | --- |
| Alpha Acids | 64 | 1.00 |
| Isoalpha Acids | 39 | 1.00 |
| Tetrahydroisoalpha Acids | 55 | 1.00 |
| Rhoisoalpha Acids | 62 | 1.00 |
| Beta Acids | 26 | 1.00 |
| Beta Acids | 73 | 0.50 |
| Beta Acids | 100 | 0.33 |
| Standard Control | 0 | — |
| Untreated Control | 100 | — |

Control of hop powdery mildew using hop acids was best with beta acids at a concentration of 1% where the incidence was 26% that of the untreated plants. The standard control, however, was better with an incidence of zero. The other hop acids and beta acids at lesser concentrations produced less control.

Potato Late Blight Control Tests

The late blight organism is the fungus *Phytophthora infestans* and the host plant is potato, *Solanum tuberosum*. Tests were conducted in a greenhouse in Pullman, Wash. Young potato plants were sprayed with the treatments and after the treatments dried, the plants were sprayed with a water suspension containing spores of the disease. Disease incidence and severity were determined six days after inoculations. Treatments were replicated four times. Standard control was the fungicide Chlorothalonil (Bravo). Percent incidence is the percent of leaves showing symptoms. Percent severity is the portion of each leaf surface showing symptoms.

| Treatment | Percent Incidence | Percent Severity | Percent Concentration |
| --- | --- | --- | --- |
| Beta Acids | 0 | 0 | 1.00 |
| Standard Control | 0 | 0 | — |
| Untreated Control | 100 | 100 | — |

Beta acids at 1% and the standard control fungicide gave complete control of the potato late blight organism in the greenhouse.

Hop Downy Mildew Control Tests

The hop downy mildew organism is the fungus *Pseudoperonospora humuli* and the host plant is hop, *Humulus lupulus*. Tests were conducted in a growth chamber in Yakima, Wash. Young hop plants with eight pairs of leaves were used for testing. Test plants were sprayed with a treatment using a spray bottle with a pull trigger. After the treatment dried, powdery mildew spores suspended in water were sprayed onto the test leaves with a spray bottle. Inoculated plants were incubated in a greenhouse for seven days and then lesions were counted on one pair of leaves per plant. Treatments were replicated four times. Standard control was copper. Percent incidence is the average number of lesions per leaf on ten inoculated leaves expressed as a percent of the untreated control.

| Treatment | Percent Incidence | Percent Concentration |
| --- | --- | --- |
| Alpha Acids | 12 | 1.00 |
| Isoalpha Acids | 4 | 1.00 |
| Tetrahydroisoalpha Acids | 6 | 1.00 |
| Rhoisoalpha Acids | 5 | 1.00 |
| Beta Acids | 6 | 1.00 |
| Standard Control | 5 | — |
| Untreated Control | 100 | — |

All hop acids treatments produced good control of the hop downy mildew organism in the greenhouse. Disease incidence in the hop acids tests was similar to that of the standard control product.

Grapevine Powdery Mildew Control Tests

The grapevine powdery mildew organism is the fungus *Erysiphe* (=*Uncinula*) *necator* and the host plant is wine grape plant *Vitis vinifera*. Tests were conducted in an experimental vineyard near Pasco, Wash. Treatments were applied using an airblast sprayer at a volume of 100 gallons per acre. Disease inoculum was natural and had been the heaviest it has been in at least seven years. Plot size was five grape plants. Treatments were replicated four times and evaluations were made on September $4^{th}$. Standard control was the fungicide Fenarimol (Rubigan). Percent incidence is the percent of grape clusters that showed disease. Percent severity is the portion of each grape cluster that was covered with symptoms.

| Treatment | Percent Incidence | Percent Severity | Percent Concentration |
| --- | --- | --- | --- |
| Beta Acids | 51 | 11 | 1.00 |
| Standard Control | 71 | 23 | — |
| Untreated Control | 100 | 94 | — |

Beta acids treatment limited the incidence of powdery mildew on grape clusters to 51% while the industry standard allowed 71% compared to the 100% incidence in the untreated plots. Severity was substantially reduced by both treatments compared to the untreated control.

Twospotted Spider Mite Control Tests

The pest organism is *Tetranychus urticae* (twospotted spider mite). Test for efficacy of hop acids on this organism were conducted in a laboratory near Prosser, Wash. Tests were conducted by spraying the treatments onto one inch in diameter leaf disks cut from Dwarf Bean, *Phaseolus vulgaris*. Each leaf disk contained 25 spider mites feeding on the leaf. Two milliliters of treatment were applied to each leaf disk using a Potter Precision Spray Tower. Leaf disks were evaluated to determine efficacy 48 hours after spraying. Treatments were replicated three times. Percent live mites were the percent of mites still alive 48 hours after treatment.

| Treatment | Percent Live Mites | Percent Concentration |
| --- | --- | --- |
| Alpha Acids | 0 | 1.25 |
| Alpha Acids | 15 | 0.62 |
| Alpha Acids | 50 | 0.31 |
| Beta Acids | 0 | 0.31 |
| Beta Acids | 13 | 0.16 |
| Beta Acids | 30 | 0.08 |
| Isoalpha Acids | 0 | 0.15 |
| Tetrahydroisoalpha Acids | 0 | 10.00 |
| Tetrahydroisoalpha Acids | 65 | 5.00 |
| Untreated Control | 100 | — |

| Tetrahydroisoalpha Acids | 65 | 5.00 |
| --- | --- | --- |
| Untreated Control | 100 | — |

There were no live mites with the alpha acids treatment at 1.25% concentration and no live mites with the beta acids emulsion as low as 0.31%.

B. Subsequent Field Tests.

A confidential field trial was conducted using 1.0% beta acids as an emulsion to determine if this formulation could be efficacious in the field against the twospotted spider mite.

1. Field Test Methods.

Starting material was the 10.0% aqueous beta acids solution. Product was mixed with other ingredients in the sprayer tank in a specific order to prevent formation of a nozzle-plugging film that can develop when the 10.0% aqueous beta acids solution is diluted with hard water. Preparation of each 100 gallons of 1.0% beta acids emulsion require first loading 88.5 gallons of water into the sprayer tank followed by the addition of one-half gallon of liquid soap. The liquid soap is necessary to prevent the film from developing when the beta acids is added to the water. After the soap is added, one gallon of crop oil is added followed by addition of three ounces of a defoamer. Finally, ten gallons of the 10.0% aqueous beta acids solution is added to the tank. Final concentrations of each component of the tank mix are: one-half percent liquid soap, one percent crop oil and one percent beta acids.

This mixture was applied to hop plants using a Windmill 400 gallon airblast sprayer. The mixture was applied to a one-acre test plot at the rate of 20 gallons per acre and to another one-acre plot at the rate of 100 gallons per acre. A total of five applications were made during the growing season. The first was made June $9^{th}$ and the final on August $1^{st}$.

Counts of live spider mites were made periodically during the season to monitor the effect of the product on the number of live mites. Simultaneously, the beneficial predator mites *Galendromus occidentalis* and *Neoseiulus fallacis* were counted to determine the effect of the product on these predator mites since these predator mites are useful in helping to reduce the numbers of twospotted spider mites. For a comparison to the standard chemical control of spider mites in the field, a one-acre test plot was treated with standard chemicals and monitored for spider mite numbers. Standard chemicals used for mite control were avermectin-B (Agrimek) and bifenazate (Acramite).

2. Field Test Results.

About mid-way through the growing season, on July $8^{th}$, mite counts were similar in all three of the monitored plots with 7-13 mites per leaf. By July $22^{nd}$, the numbers in the standard plot had reduced to near zero after a standard chemical application while numbers were still at 15-20 in the beta acids treated plots. However, throughout this same period, the predator numbers were quite high in the beta acids treated plots while being at zero in the standard treated plot. By August $12^{th}$, the mite numbers in the beta acids treated plots also came to near zero, partly from the treatment with beta acids and partly from the help of the high populations of the predator mites for which the beta acids has the effect of preserving. Mite populations in the beta acids treated plots, after approaching zero on August $12^{th}$, remained near zero for the rest of the season. Predator populations in the standard plot were at zero for the entire season, while in the beta acids treated plots, the predator numbers reached as high as 12 per leaf before eventually dropping off to zero as their food source (spider mites) eventually disappeared by August $12^{th}$ in the beta acids treated plots. Results of these field applications are shown in the following graphs.

C. Follow-Up Tests.

At the 1% emulsion concentration, beta acids have shown good suppression of spore formation in hop powdery mildew colonies that were already formed. This is an important development because it can be used to suppress powdery mildew infections that are already in existence in a hop field.

Additional tests are being conducted to other pests that can be controlled using hop acids. What is considered to be the invention is not to be limited by the above examples or data. Instead, the invention is to be limited only by the following claims, which are to be interpreted according to established doctrines of claim interpretation. In addition to other definitions given above, the terms "hop acids," "solution," and "emulsion" are to be interpreted as used above and as they are understood in the hop industry.

What is claimed:

1. A method for controlling spider mites on plants, the method consisting essentially of applying an aqueous emulsion of hop acids comprising at least about 0.62% hop alpha acids or at least about 0.08% hop beta acids to a plant to control spider mites, wherein the emulsion is free of any other pesticidal active agent, and wherein hop acids are the sole emulsifier present in the aqueous emulsion.

2. The method of claim 1, wherein the emulsion comprises at least 1.0% hop alpha acids.

3. A method for controlling spider mites on plants, the method comprising applying an aqueous emulsion of hop alpha acids comprising at least about 0.62% hop alpha acids to a plant to control spider mites, wherein the emulsion is produced by mixing hop extract at 55-70° C. with water at pH 6-8, separating the aqueous phase, and diluting the aqueous phase to form a stable aqueous emulsion, wherein the aqueous emulsion is free of other pesticidal agents.

4. A method for controlling spider mites on plants, the method consisting essentially of applying an aqueous emulsion of hop acids, wherein the emulsion comprises at least 0.15% concentration of hop isoalpha acids to a plant to control spider mites, wherein the emulsion is free of any other pesticidal active agent, and wherein hop acids are the sole emulsifier present in the aqueous emulsion.

5. A method for controlling spider mites on plants, the method comprising applying an aqueous emulsion of hop beta acids comprising at least about 0.08% hop beta acids to a plant to control spider mites, wherein the emulsion is produced by preparing an aqueous solution of hop alpha or hop beta acids and mixing the solution with water to form an aqueous emulsion, wherein the aqueous emulsion is free of other pesticidal agents.

6. A method for controlling spider mites on plants, the method comprising applying at least about 1.25% hop alpha acids or at least about 0.31% hop beta acids as an aqueous emulsion to a plant to control spider mites, wherein the emulsion is produced by preparing an aqueous solution of hop alpha or hop beta acids and mixing the solution with water to form an aqueous emulsion, wherein the aqueous emulsion is free of other pesticidal agents.

7. A method for controlling spider mites in an agricultural crop, the method consisting essentially of applying an aqueous emulsion comprising at least 1.0% hop beta acids to the agricultural crop, thereby controlling spider mites, wherein the emulsion is free of any other pesticidal active agent, and wherein hop acids are the sole emulsifier present in the aqueous emulsion.

8. A method for controlling spider mites on plants, the method comprising applying an aqueous emulsion of hop acids, wherein the emulsion is produced by preparing an aqueous solution of hop alpha or hop beta acids and mixing the solution with water to form an aqueous emulsion comprising at least about 0.62% hop alpha acids or at least about 0.08% hop beta acids as the sole active agent, and wherein said hop acids are the sole emulsifier present in the aqueous emulsion, wherein the aqueous emulsion is free of other pesticidal agents.

9. A method for controlling downy mildew on plants, the method comprising applying at least about 1% hop alpha acids or at least about 1% hop beta acids to a plant as an aqueous emulsion to control downy mildew, wherein the emulsion is free of any other pesticidal active agent, and wherein hop acids are the sole emulsifier present in the aqueous emulsion.

10. A method for controlling powdery mildew on plants, the method comprising applying at least about 1% hop beta acids to a plant to control powdery mildew, as an aqueous emulsion, wherein the emulsion is free of any other pesticidal active agent, and wherein hop acids are the sole emulsifier present in the aqueous emulsion.

11. A method for controlling late blight organisms on plants, the method comprising applying an aqueous emulsion of hop beta acids comprising at least about 1% hop beta acids to a plant to control late blight organisms, wherein the emulsion is produced by preparing an aqueous solution of hop beta acids and mixing the solution with water to form an aqueous emulsion, wherein the aqueous emulsion is free of other pesticidal agents.

12. A method for controlling late blight organisms on plants, the method comprising applying an aqueous emulsion of hop beta acids comprising at least about 1% hop beta acids to a plant to control late blight organisms, wherein the emulsion is produced by mixing hop extract at 55-70° C. with water at pH 10-11, separating the aqueous phase, and diluting the aqueous phase to form a stable aqueous emulsion, wherein the aqueous emulsion is free of other pesticidal agents.

* * * * *